United States Patent
Hart

(12) 
(10) Patent No.: US 6,479,247 B1
(45) Date of Patent: *Nov. 12, 2002

(54) DENDRITIC CELL-SPECIFIC ANTIBODIES

(75) Inventor: Derek N. J. Hart, Brisbane (AU)

(73) Assignee: The Corporation of the Trustees of the Order of the Sisters of Mercy in Queensland, Queensland (AU)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/284,249

(22) PCT Filed: Oct. 9, 1997

(86) PCT No.: PCT/NZ97/00134

§ 371 (c)(1),
(2), (4) Date: Apr. 29, 1999

(87) PCT Pub. No.: WO98/15579

PCT Pub. Date: Apr. 16, 1998

(30) Foreign Application Priority Data

Oct. 9, 1996 (NZ) ................................................ 299537

(51) Int. Cl.[7] .......................... C07K 16/28; C07K 16/44; C07K 16/00; C12N 5/20; G01N 33/577
(52) U.S. Cl. .............................. 435/7.21; 435/2; 435/7; 435/7.1; 435/7.24; 435/334; 435/343; 435/343.1; 435/975; 436/512; 436/536; 935/104; 935/108; 530/300; 530/350; 530/387.1; 530/387.2; 530/388.2; 530/388.22; 530/388.7; 530/388.73; 530/389.1; 530/389.6; 530/391.1; 530/391.3; 424/130.1
(58) Field of Search ........................... 435/2, 7.1, 7.21, 435/7.24, 975, 343, 343.1, 334; 424/130.1; 436/512, 536; 935/104, 108; 530/380, 388.2, 388.22, 388.7, 388.73, 389.1, 389.6, 391.1, 391.3, 359, 387.1, 387.2

(56) References Cited

U.S. PATENT DOCUMENTS 4,281,061 A * 7/1981 Zuk et al. ........................ 435/7
5,876,917 A * 3/1999 Hart ................................ 435/2

FOREIGN PATENT DOCUMENTS

WO    WO A 9512409    5/1995    .......... A61K/39/00
WO    WO 95/15340    * 6/1995    ........... C07K/16/28

OTHER PUBLICATIONS

Starling et al., "A novel member of the immunoglobulin gene superfamily recognized by the mAb CMRF–35.", Chemical Abstracts, vol. 12, No. 10, 1997, 130446f, 1995.*

Hock et al., "characterization of CMRF–44, a novel monoclonal antibody to an activation antigen expressed by the allostimulatory cells within peripheral blood, including dendritic cells.", Immunology, 83, 1994, pp. 573–581, 1994.*

Cheimcal Abstract 126 130446, Columbus Ohio "A novel member of the immunoglobulin gene superfamily recognized by the mAb CMRF–35" Starling, Gary C.; Daish, Angela; Daniel, Philip B.; Jackson, David G.

Starling et al, "A novel member of the immunoglobulin gene superfamily . . . ," Leucocyte Typing V: White Cell Differ. Antigens, Proc. Int. Workshop Conf., 5th (1995), Meeting Date 1993, vol. 1, 1166–1167.

* cited by examiner

Primary Examiner—Christopher L. Chin
Assistant Examiner—Lisa V Cook
(74) Attorney, Agent, or Firm—Nixon & Vanderhye

(57) ABSTRACT

Isolated antibody or preparation of antibodies comprising an antigen-binding domain wherein the antigen is present on activated dendritic cells and wherein the antibody does not interact with CMRF-44 antigen or CD83 antigen.

7 Claims, 10 Drawing Sheets

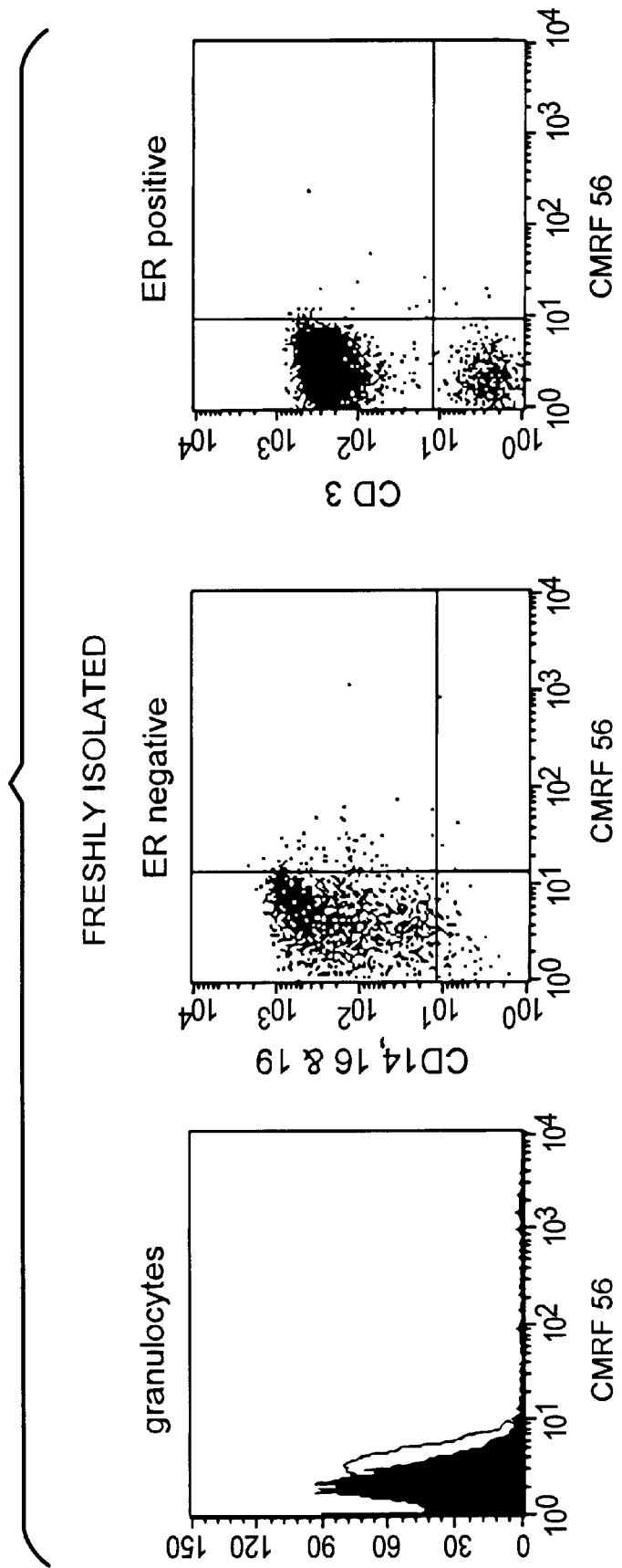

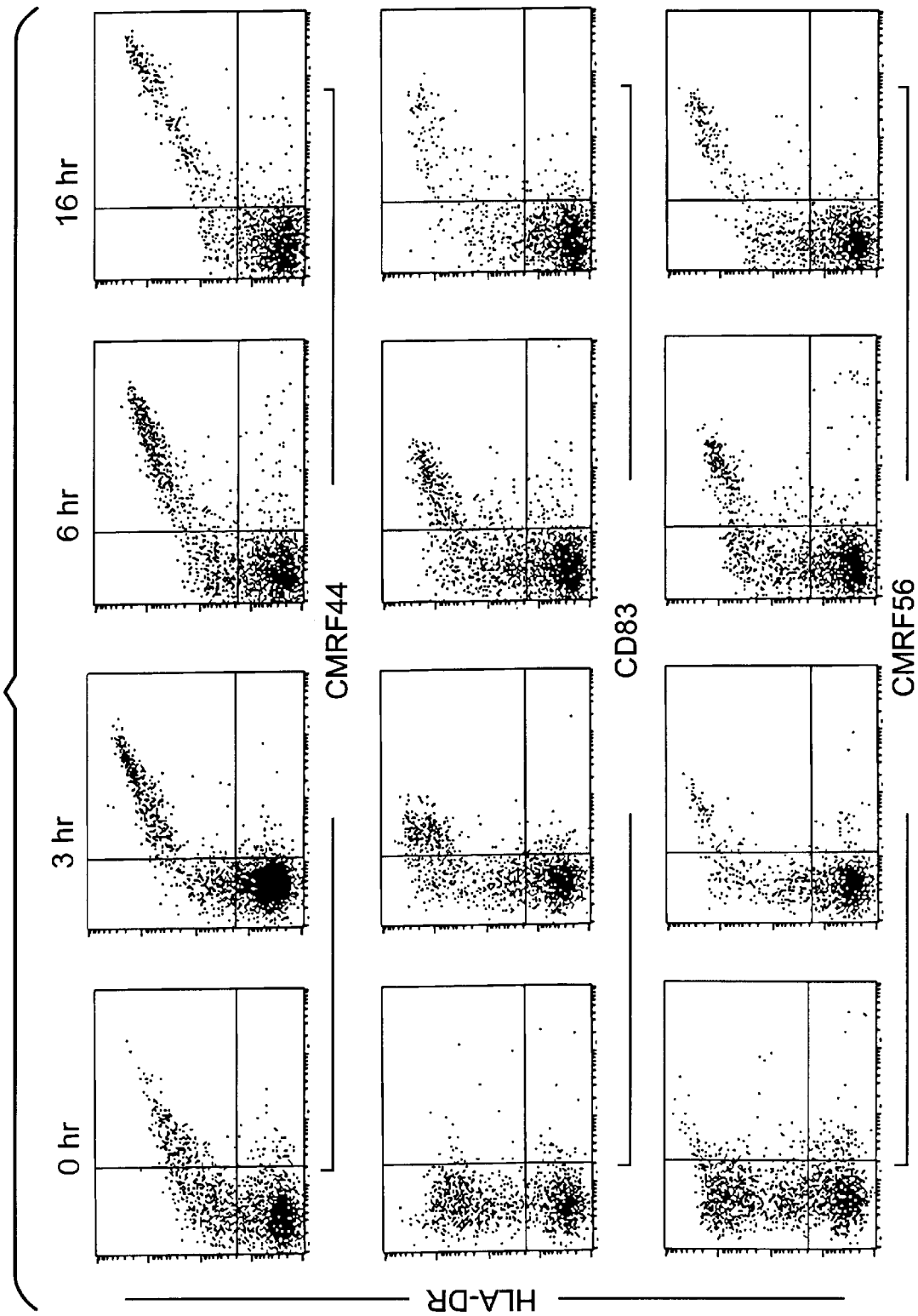

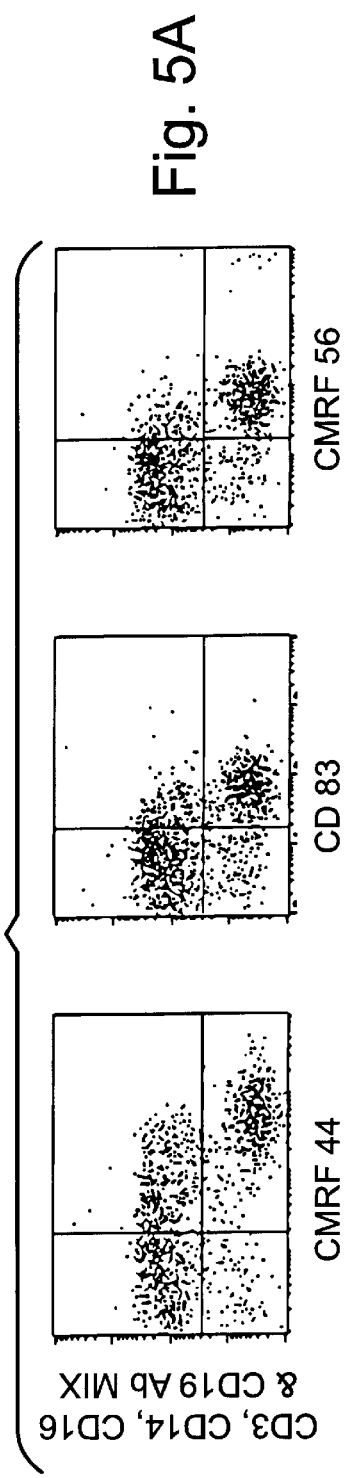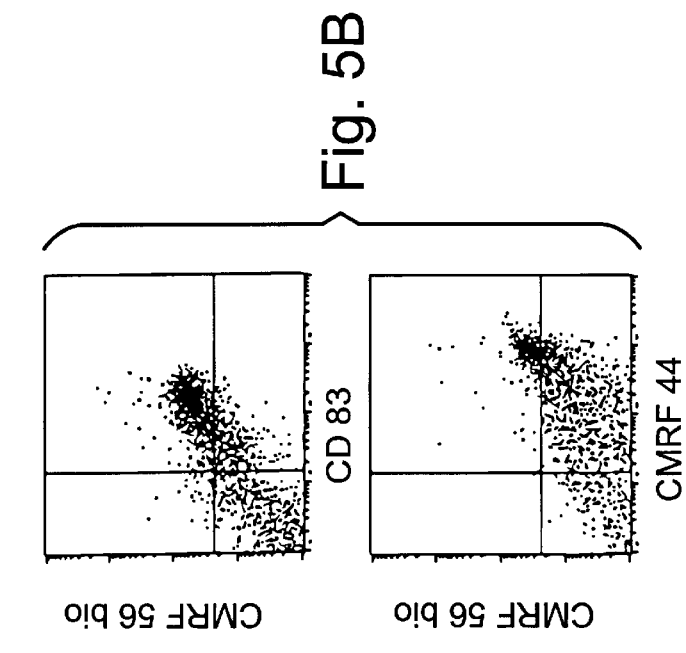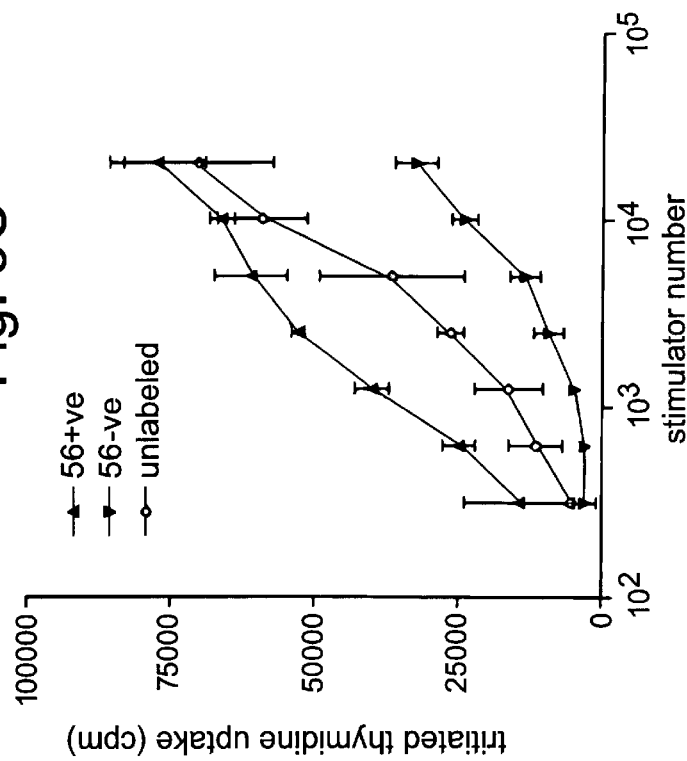
Fig. 5A
Fig. 5B
Fig. 5C

SEQUENCE LISTING

```
<160> NUMBER OF SEQ ID NOS: 4

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence:Made in lab

<400> SEQUENCE: 1
cccaagctta tgtcgcgcgg cctccag                                       27

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence:Made in lab

<400> SEQUENCE: 2
gcgaattcac ttacctgtct ccgctctgta tttctt                             36

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:Made in lab

<400> SEQUENCE: 3
gaagatctac gccggaggtg aaggtg                                        26

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:Made in lab

<400> SEQUENCE: 4
gaagatctct ccgctctgta tttctt                                        26
```

DENDRITIC CELL-SPECIFIC ANTIBODIES The present application is a 371 of PCT/NZ97/00134, filed Oct. 9, 1997, and claims priority from New Zealand patent application Serial No. 299537, filed Oct. 9, 1996.

FIELD OF THE INVENTION

This invention relates generally to immunological reagents (antibodies) capable of binding to activated dendritic cells, to cell lines which express such antibodies and to a process for identifying and purifying dendritic cells from blood using such antibodies.

BACKGROUND OF THE INVENTION

Dendritic cells (DC) constitute a distinct group of potent antigen presenting cells (APC) which are bone marrow derived and found as trace populations in the circulation as well as within both lymphoid and nonlymphoid tissues[1-3]. Although their importance as the most effective haemopoletic cell involved in the initiation of primary immune responses has been well demonstrated[4-7], no human DC specific lineage marker has been identified and most features of their ontogeny and relationship to other leukocytes remains unclear.

Phenotypically, human DC are characterised[1-3,7-11] by a high density of class II MHC antigens, the presence of a wide range of adhesion molecules and the absence or low expression of a range of lineage specific cell surface antigens (CD3, CD14, CD16, CD 19, CD57). A number of activation antigens including IRAC[12], HB15[13], 4F2[8], IL-2R[7,8], and B7/BB-1[7,14] have also been reported on human DC, particularly after activation, although the anti-IRAC and HB15 reagents have not been shown to stain isolated fresh blood DC. Despite this phenotypic characterisation, identification and therefore purification of DC remains difficult as the majority of these antigens are expressed by other resting and activated cell types. Many of the functional and phenotypic features of DC are shared by both Hodgkins cells (HC) and Hodgkins Disease (HD) derived cell lines and there is increasing evidence to support the hypothesis, that in some instances, HC represent a malignant form of DC[15-17].

Immunological reagents for use in a process for identifying and purifying DC therefore have obvious utility. Such reagents will need to recognize epitopes or antigens specific to DC. To date antibodies have been generated against early activation antigens CD83[18,19] and CMRF-44[20]. However, there remains a need to have available antibodies which can bind to different epitopes on DC than CD83 and CMRF-44.

It is therefore an object of this invention to provide immunological reagents which recognise epitope(s) of a novel activation antigen found on DC or at least provide the public with a useful choice.

SUMMARY OF THE INVENTION

In a first aspect the present invention can be said to provide antibodies or binding fragments thereof which specifically bind to DC activation antigen CMRF-56.

Conveniently, the antibody is a monoclonal antibody, preferably monoclonal antibody CMRF-56 (mAb CMRF-56).

In yet a further aspect, the invention provides hybridoma cell line CMRF-56.

In still a further aspect, the present invention provides mAb CMRF-56 secreted by hybridoma cell line CMRF-56 which specifically binds to an epitope on activated human DC but does not bind to activation antigens CMRF-44 and CD83.

In yet a further aspect, the invention provides an antibody or antibody binding fragment which is specific for the epitope on human DC to which mAb CMRF-56 binds.

In still a further aspect, the present invention provides a process for identifying activated DC in a sample containing such cells comprising the step of contacting said sample with an antibody or antibody binding fragment as defined above.

In yet a further aspect, the invention provides a process for purifying and/or concentrating DC from a sample containing such cells comprising the step of contacting said sample with an antibody or antibody binding fragment as defined above.

In the preferred embodiment of these processes, the cells to be identified or purified are activated human DC and the antibody is mAb CMRF-56.

In still a further aspect, the invention provides a DC purification system for use in purifying or concentrating DC from a sample containing such cells which includes an antibody or antibody binding fragment as defined above.

Conveniently, the purification system is designed to purify activated human DC and the antibody is optionally labelled mAb CMRF-56.

In still a further aspect, the present invention consists in activated DC recovered by a process as defined above or by using a purification system as defined above.

In yet a further aspect, the invention provides an immunopotentiating composition comprising activated DC obtained as above and at least one antigen capable of generating a protective immunological response to a disease in an animal susceptible to such disease.

In still a further aspect, the invention provides an immunopotentiating composition comprising an antibody as defined above and at least one antigen capable of generating a protective immunological response to a disease in a patient susceptible to such disease.

In still a further aspect, the invention provides an immunopotentiating composition comprising activated DC obtained as above, an antibody as defined above and at least one antigen capable of generating a protective immunological response to a disease in a patient susceptible to such disease.

In still a further aspect, the invention provides an immunopotentiating composition comprising an antibody as defined above.

In still a further embodiment, the invention provides a method of prophylaxis and/or therapy in relation to a disease which comprises administering to a subject susceptible to said disease an immunopotentiating composition as defined above.

In yet a further aspect, the invention provides an assay kit which includes mAb CMRF-56 for use as a diagnostic marker of activated DC.

SUMMARY OF THE DRAWINGS

While the present invention is broadly as defined above, it will be appreciated that it is not limited thereto but that it also includes embodiments of which the following description provides examples. In addition, the present invention will be better understood by reference to the accompanying drawings which are as follows:-

FIG. 4 shows expression of CMRF-56 on directly isolated DC. (A) Directly isolated blood DC were cultured in medium for 0, 3,6 or 12 h then analysed by double labelling with CMRF-56, CMRF-44 or CD83 vs DR-PE. In all cases the gates delineating positive staining shown were set on the basis of negative control staining. Data are from a representative experiment of 3 performed.

FIG. 5 shows an analysis of CMRF-56 expression within cultured low density preparations of ER⁻BMC (A) Dot plots of preparations double labelled with CMRF-44, CD83 or CMRF-56 vs a mix of PE conjugated CD3, CD14, CD16 and CD19 mAb (B) Dot plots of preparations double labelled with CD83 or CMRF-44 vs CMRF-56 biotin. in all cases the gates delineating positive staining shown were set on the basis of negative control staining. (C) Allogeneic MLR performed following sorting of a low density preparation on the basis of CMRF-56 expression. The CMRF-56 positive (Δ) and negative (∇) populations together with unlabelled (◇) and labelled but not sorted controls were cultured with allogeneic T lymphocytes for 5 days then ($^3$H) TdR incorporation determined. Results are expressed as the mean of triplicate counts" SEM. Data are from a representative experiment of three performed.

DESCRIPTION OF THE INVENTION

Figure 1B:
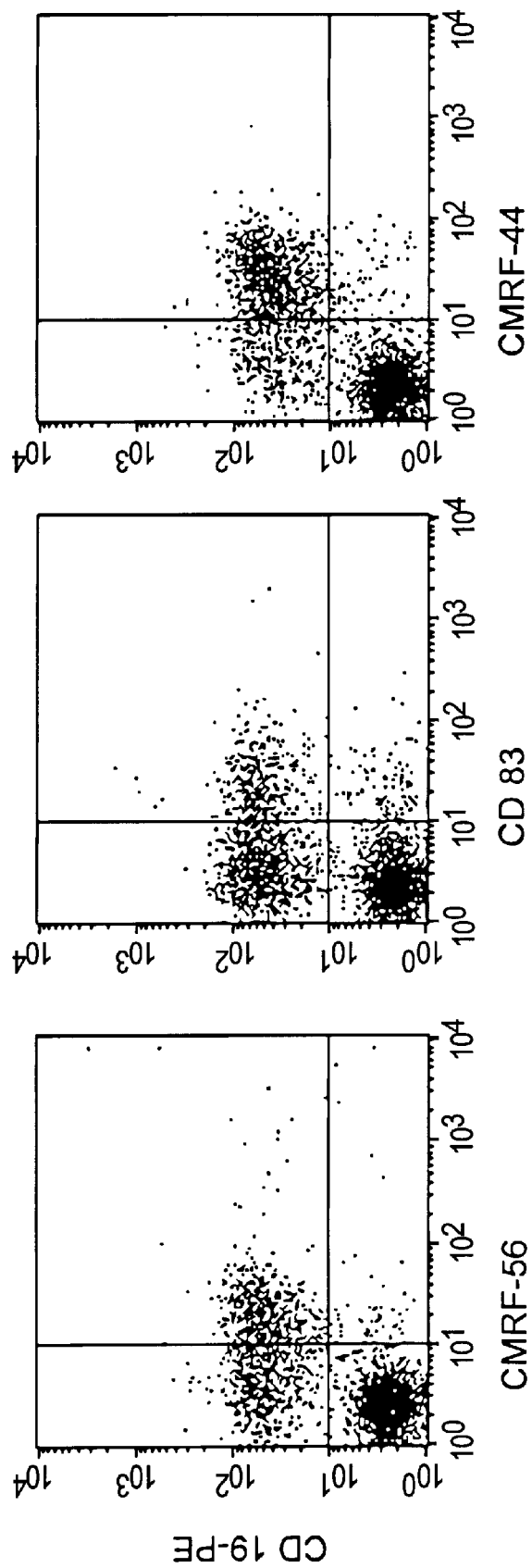
FIG. 1 shows the reactivity of mAb CMRF-56 with blood and tonsil leukocytes. (A) (i) Fluorescent intensity histogram of granulocytes stained with mAb CMRF56(filled) or isotype control (ii) dot plots of ER⁻PBMC double labelled with CMRF-56 vs CD3, CD14, CD16, CD19-PE (iii) dot plot of ER⁺PBMC double labelled with CMRF56 vs CD3-PE. (B) Dot plots of cultured (16 h. 37° C.) ER⁻PBMC double labelled with CMRF-56, CD83 or CMRF-44 vs CD19-PE. (C) Dot plots of tonsil ER⁻ lymphocytes double labelled with CMRF-56, CD83 or CMRF-56 vs CD19-PE. In all cases the gates delineating positive staining shown were set on the basis of negative control staining. Data are from representative experiments.

As indicated above, in a primary aspect the present invention provides immunological reagents (antibodies) capable of specifically binding to activated DC. The antibodies bind to a novel activation antigen on DC which has been called CMRF-56 antigen.

It will be appreciated that the antibodies which bind activation antigen CMRF-56 can be in the form of antisera containing polyclonal antibodies or, as is preferred. monoclonal antibodies may be obtained by use of hybridoma technology. Still further, antibodies or binding fragments can be produced using biochemical or recombinant DNA techniques.

It is most desirable for the immunological reagents of the invention to be monoclonal antibodies or binding fragments of such antibodies. The general procedure of Kohler and Milstein[21] is therefore used. Generally, this procedure involves obtaining antibody-producing cells from the animal and fusing the antibody-producing cells with strains of myeloma cells to produce hybridomas. These hybridomas are grown or cultured to produce monoclonal antibodies specific for dendritic cells.

An example of the procedure using myeloma cell line NS-1 is given below. Cell line NS-1 is obtainable from Professor C Milstein, MRC Laboratory of Molecular Biology, Hills Road, Cambridge CB2 2QH, United Kingdom.

Other myeloma cell lines are known in the art and include, for example, the following cell lines: X63Ag8 653, SP2/0, FO and NSO/1. Cell lines which neither synthesize nor secrete immunoglobulin heavy or light chains (eg SP2/0) are generally preferred to cell lines which synthesise but do not secrete, immunoglobulin chains.

If desired, antibody fragments can be prepared by controlled protease digestion of whole immunoglobulin molecules as described in Tjissen[22].

Alternatively, antibody fragments can be prepared using molecular biological techniques by isolating, from hybridoma cells, the genetic material encoding the variable regions of the heavy, light or both chains of the monoclonal antibodies and expressing them in suitable organisms for the product of recombinant antigen binding fragments-(Fv, ScFv, Fab etc.) of the monoclonal antibody[23].

By way of illustration of the invention, the generation and characterisation of a monoclonal antibody, designated mAb CMRF-56, capable of binding to an epitope on an activation antigen CMRF-56 of human dendritic cells will now be described. From this description, those persons skilled in this art will also appreciate how other antibodies (or their binding fragments) which bind to activation antigen CMRF-56 can be obtained for use in the extraction of human DC or DC from other animals.

METHODS

Monoclonal Antibodies and Immunolabelling

The monoclonal antibodies CMRF-15 (erythrocyte sialoglycoprotein, IgM), CMRF31 (CD14, IgG2a), CMRF- 44 (IgM) and biotinylated CMRF-44 were produced in this laboratory. HB15a (CD83, IgG2b) was a gift from Dr T Tedder, Duke University, North Carolina. The CD19 mAb FMC63 (IgG2a) and the isotype control mAb X63 (IgG 1), Sal4 (IgG2b) and Sal5 (IgG2a) were a gift from Prof H Zola (Flinders Medical Centre, Adelaide, Australia). The CD1a mAb NaI/34 was a gift from Prof A McMichael (Institute of Molecular Medicine, Oxford, UK). HuNK-2 (CD16, IgG2a) was a gift from Prof I McKenzie (Austin Research Institute, Melbourne, Australia. OKT3 (CD3, IgG2a). HNK-1 (CD57, IgM) and OKM1 (CD11b, IgG1) were produced from hybridomas obtained from the ATCC. Phycoerythrin conjugated antibodies to CD3(leu4, IgG1), CD14 (leuM3, IgG2b), CD16(leu11c, IgG1), CD19 (leuM12, IgG1) and HLA-DR (L243, IgG2a) antigens were purchased from Becton Dickinson, Mountain View, Calif. Flourescein isothiocynate conjugated sheep anti-mouse (FITC-SAM) was purchased from Silenus, Hawthorn, Australia. Labelling was carried out on ice using standard techniques. Briefly, cells were incubated with primary antibody (30 min), washed then incubated with FITC-SAM prior to further washing and analysis. Double labelling of mAb/FITC-SAM labelled cells was carried out following a further incubation of cells in 10% mouse serum for five minutes followed by addition of PE conjugated or biotinylated second antibody. For biotinylated antibodies a further washing step was followed by incubation (30 min) with avidin-PE (Becton Dickinson). Cells were analysed or sorted on a FACS Vantage (Becton Dickinson). Samples that could not be analysed immediately were fixed in 1% paraformaldehyde and stored at 4° C.

To study capping of the relevent antigens, L428 cells were labelled with either sal4 or HB15/PE-SAM then incubated at 37° C. for 60 min. Cells were then washed at 4° C., then labelled (on ice) with either CMRF-56-FITC, L243-FITC, X63-FITC or FITC-SAM.

Generation of the CMRF-56 mAb

A balb/c mouse was immunised with the HD-derived cell line L428 and the splenocytes fused with the myeloma line NS-1 four days later. The CMRF-56 hybridoma was cloned thrice by limiting dilution and used to generate ascites fluid. Isotyping was performed using an indirect ELISA kit (Sigma, St.Louis, Mo.). Purified CMRF-56 was prepared utilising Protein A chromatography, and biotinylated using Biotin-X-NHS (Calbiochem, La Jolla, Calif.). Briefly CMRF-56 at 2 mg/ml in 0.05 M $NaHCO_3$ (pH 8.5) was incubated with Biotin-X-NHS (7.5 ug/ml, Calbiochem, La Jolla, Calif.) for 30 min (RT) prior to dialysis.

Cell Lines

T cell lines (HSB-2, Molt 4 and Jurkat), EBV transformed B cell lines (WT49, Mann). Burkitt's lymphoma lines (Raji and Daudi), pre-B (Nalm 6), myeloerythroid (K562) and monocytoid leukemia (HL60, U937, KG1, KG1a, THP-1, HEL) leukemia cell lines were grown in medium (10% FCS (Irvine Scientific, Santa Anna, Calif.) in RPMI1640 (Gibco, Auckland, New Zealand) supplemented with 2 mM glutamine, 0.06 g/l penicillin and 0.1g/l streptomycin). The Hodgkins cell line L428 was obtained from Dr V Diehl (Clinik for Innere Medizine, Cologne, Germany) and the Hodgkins cell lines KM-H2 and HDLM-2 (grown in 20% medium) were obtained from Dr H G Drexler (German Collection of Micro-organisms and Cell Cultures, Braunschweig, Germany).

Lymphocyte, Granulocyte and Monocyte Preparation

Blood was obtained from volunteer donors with appropriate informed consent according to Ethical Committee guidelines. Peripheral blood mononuclear cells (PBMC) were prepared by centrifugation over sterile Ficoll/Hypaque (d=1.077g/cm$^3$, Pharmacia, Uppsala, Sweden) gradients. T lymphocyte-enriched fractions (ER$^-$) and non-T fractions (ER$^-$)were prepared from PBMC by resetting with neuraminidase treated sheep erythrocytes as described previously[34]. Granulocytes were prepared from peripheral blood following dextran sedimentation of RBC as described previously[34]. Activated T lymphocytes were prepared by culture of ER$^+$PBMC ($2\times10^6$/ml) in medium supplemented with either 5 ug/ml PHA (Sigma) or the phobol ester phorbol 12—myristate 13 acetate (PMA, Sigma) at 25 ng/ml plus the calcium ionophore A23187 (Sigma) at 500 ng/ml.

ER$^-$PBMC were used as an enriched source of monocytes. Activated monocytes were obtained by culture of ER$^-$PBMC ($2\times10^6$/ml) in medium supplemented with either IFNγ (500 U/ml, a gift from Boehringer Ingelheim, Germany), bacterial LPS (100 ng/ml), TNFα (20 ng/ml) or GM-CSF (500 u/ml, Novartis). Monocyte populations were monitored by double labelling with CD14-PE.

The effectiveness of the in vitro activation was determined by monitoring by flow cytometry changes in the expression of the activation antigens CD25, CD71, HLA-DR and CMRF-44.

Dendritic Cell Preparation

Highly enriched DC populations were prepared using established laboratory methods:

i) Resting DC were prepared by direct immunodepletion[33,34]. Briefly ER$^-$PBMC were labelled with a mix of CD3, CD11b, CD14, CD16 and CD19 mAb. After incubation with MACS magnetic microspheres (Miltenyi Biotech, Germany) labelled cells were removed by magnetic immunodepletion and the mAb negative cells were then labelled with FITC-SAM and further purified by FACS sorting. In a number of experiments resting DC were then cultured (37° C., 5% $CO_2$) in medium ($2\times10^6$/ml) prior to analysis.

ii) Cultured low density blood DC were prepared from cultured (16 h. 37° C., 5% $CO_2$) ER$^-$PBMC[36]. The low density fraction was then isolated by centrifgation over a Nycodenz (Nycomed Pharma, Norway) gradient[36] and used either directly as a DC enriched (10–30%) fraction or further purified by immunodepletion as described above.

iii) LC and dermal DC were isolated[33] from skin (obtained with consent) separated into epidermal sheets and dermis by overnight digestion (4° C.) with dispase (0.25% in PBS, Boehringer-Mannheim). Epidermal cell (EC) suspensions were produced by disaggregation of the tissue through a cell dissociation cup (grade 40 mesh, Sigma) in the presence of 0.25% Typsin (Sigma). Fresh LC were enriched (2–15%) at this stage by lymphoprep gradient as described[37]. Dermal cell suspensions were obtained from dermal sheets by incubation (1 h, 37° C.), with collagenase D (Boehringer-Mannheim, 1 mg/ml) and DNAase I in medium. A single cell suspension was obtained by filtering through nylon mesh (80 μm) and following centrifugation over a lymphoprep gradient (d=1.077 g/cm$^3$, 10 min, 500×g) the low density fraction were utilised as an enriched (30–50%) dermal DC population.

iv) Synovial fluid DC (SFDC) were isolated as previously described[38]. Following informed consent SF was collected by routine knee joint aspirations from patients with chronic arthritis into EDTA blood tubes. ER$^-$ cells were labelled with a mix of mAb against CD3, CD14, CD15, CD16 and CD19 and depleted using immunomagnetic MACS beads as described above for preparation of blood DC. Residual labelled cells were further depleted using a FACS. The remaining unlabelled MHC class II positive cells constituted the SFDC population.

v) Tonsil DC were prepared from tonsils obtained at routine tonsillectomies, following informed consent. These were processed immediately and a single cell suspension prepared by mincing the tissue finely and passing the material through a wire mesh sieve. Mononuclear cells were isolated over a F/H density gradient and Tonsil DC isolated as described above for SFDC.

vi) In vitro derived DC were generated from the adherent fraction of PBMC obtained following 2 h culture (37° C.) in Falcon 6 well plates (BD). Adherent cells were cultured in medium supplemented with GM-CSF (800 U/ml) and IL-4 (500 U/ml) for five days, whereupon TNFα was added to a final concentration of 20 ng/ml and cells cultured for a further two days before analysis.

Immunohistology

Cryostat cut en face sections (7 μm) of tonsil and lymph node (obtained with appropriate ethical permission as approved by the Canterbury Health Ethical Committee) were allowed to dry overnight, then fixed for 10 min in ice cold acetone and air dried for 30 min. Sections were incubated with 10% goat serum prior to incubation with primary monoclonal antibody (mAb) followed by biotinylated goat anti-mouse Ig (DAKO) and then addition of streptavidin-HRP (DAKO). Slides were washed 3 times with TBS between each 30 min incubation. Enzymatic activity was revealed with 3.3'-diaminobenzidine solution. After a final wash in PBS slides were counterstained (standard H&E stain) then mounted.

Immunofluorescent double labelling of acetone fixed tissue sections was carried out as described above for cell suspensions.

Functional Assays

Allogeneic MLR: $10^5$ T lymphocytes were cultured at 37° C. in 5% $CO_2$ in 96 well plates with triplicate graduated numbers of sorted APC subsets obtained from a single allogeneic donor. Wells were pulsed for 12 hours with 0.5 Ci tritiated thymidine (Amersham) immediately prior to harvest at five days. Cells were harvested onto filter paper and thymidine incorporation was measured with a liquid scintillation counter. Data are expressed as mean CPM of triplicate wells ±SD. Control wells containing T cells or APC alone incorporated <500 cpm of tritiated thymidine in all experiments.

Preparation of CD83 Transfectants

COS-7 cells grown in medium were plated on Nunc petri dishes to approximately 50% confluence. Transfection was carried out by electroporation (300 V. 500 uF) of cells ($4 \times 10^6$ in 400 ul medium) with 2 ug of CD83 plasmid (CDM8—CD83 kindly provided by Dr Tedder) or control plasmid in a biorad Gene Pulser. Cells were then cultured in medium 72 h prior to immunofluorescent analysis with the HB15a mAb to confirm CD83 expression.

Expression of CD83 Fusion Proteins

CD83-Ig was expressed in eukaryotic cells. A DNA fragment of CD83 extracellular domain (including signal peptide) was amplified from a CD83 cDNA by polymerase chain reaction (PCR) using a pair of primers (MK001:5'-CCC<u>AAG CTT</u> ATG TCG CGC GGC CTC CAG-3' (forward) (SEQ ID NO:1) and MK002:5'-GC<u>G AAT TCA</u> CTT ACC TGT CTC CGC TCT GTA TTT CTT-3' (reverse) (SEQ ID NO:2) with unique HindIII and EcoRI sites underlined). The resultant fragment was digested with EcoRI and HindIII, and ligated to EcoRI- and HindIII- digested pBluescript to generate pBS-CD83 for DNA sequencing. After confirming the DNA sequence, the fragment was excised with EcoRI and HindIII, and ligated to EcoRI- and HindIII-digested pIG vector. The vector was transfected to COS cells by electroporation, and CD83-Ig was purified from the conditioned media of the COS cells using protein A column chromatography. CD83-Histamine (CD83-Hist) was expressed in prokaryotic cells. A DNA fragment of CD83 extracellular domain (excluding signal peptide) was amplified from a CD83 cDNA by PCR using a pair of primers (MK010:5'-GA<u>A GAT CTA</u> CGC CGG AGG TGA AGG TG-3' (forward) (SEQ ID NO:3) and MK011:5'-GA<u>A GAT CTC</u> TCC GCT CTG TAT TTC TT-3' (reverse) with an unique Bgl II site (underlined). The resultant fragment was digested with Bgl II, and ligated to Bgl II-digested pQE12 to generate pQE-CD83. After confirms the DNA sequence and inframe status, the vector was used to transform XL-1 blue bacteria and CD83-Hist fusion protein was induced by adding IPTG to the bacteria culture. The fusion protein was purified from the bacteria lysate using Ni-NTA resin column chromatography.

CD83 ELISA

Binding of CMRF-56 and HB15 to CD83 constructs was analysed by ELISA. ELISA plates (Maxisorp, Nunc) were coated by incubation (37° C. 1 hr) with CD83-Ig, CD83-H or human Ig (hIg, salt precipitated) at a concentration of 10 ug/ml. Following blocking (2% BSA/PBS) wells were incubated (1 h, 37° C.) with either culture supernatant, ascites or purified mAb diluted in 1% BSA/PBS. Following washing (0.1% Tween 20/PBS) plates were incubated (1 hr, 37° C.) with GAM-HRP (Dako, 1:1500) prior to washing and colour development using o-phenylenediamine (OPD) substrate. Plates were then analysed (492 nm/650 nm) on a MRX microplate reader (Dynatech Laboratories).

Enzyme and Inhibition Studies

The enzyme susceptibility of the CMRF-56 antigen was tested by incubating (30 min, 37° C.) the cell line L428 in PBS containing either pronase (50 ug/ml, Sigma) or neuraminidase (0.1 U/ml, Behring, Marburg, Germany). Cells were washed (x3) prior to analysis by flow cytometry. The enzyme induced changes in the strength of mAb binding were determined by comparison of the MFI of treated cells with that of cells incubated in PBS alone.

N-linked glycosylation of glycoproteins was blocked by incubation (12 h. 37° C.) in medium containing either 0 or 10 ug/ml of tunicamycin (Sigma). The effect of treatment on mAb binding was determined by flow cytometry.

Immunoprecipitation

Cells were labelled using three methods (i) cell surface labelling with Biotin-X-NHS (Calbiochem)[20,39], (ii) cell surface sialic acid labelling with biotin hydrazide (Calbiochem)[40] or (iii) biosynthetically labelled with $^{35}S$ (NEN, Boston. Mass.)[20]. Following labelling cells were solubilised by incubation (1 hr on ice) of cells ($4 \times 10^7$) in 1 ml lysis buffer (100 mM Tris, 150 mM NaCl, 0.02% NaN3, pH 7.8) containing either 0.5% Triton X-100 or 0.25% CHAPS and supplemented with enzyme inhibitor Complete™ (Boehringer). Following centrifugation (10000 g, 10 min), solubilized proteins were analysed by either (i) immunoprecipitation using rabbit anti-mouse immunoglobulin covalently coupled to CNBr-activated Sepharose 4B (RAM-Sepharose) as described previously[20,39] or (ii) immunoabsorption of antigen by mAb captured on Maxsorp ELISA plates[41]. Eluted protein was analysed by gradient SDS-PAGE in combination with either autoradiography or Western blotting in combination with chemiluminescent visualisation.

Lipid extracts were prepared from L428 as described previously[20]. Slot blotting of whole cell lysates (prepared as described above) or lipid extracted material and subsequent immunostaining was carried out as described previously[20].

RESULTS

Generation of CMRF-56 mAb

Hybridomas were generated by fusion of NS-1 mycloma cells with spleen cells obtained from a mouse immunised with the HD-derived cell line L428. Hybridomas producing mAb reactive with L428 but not PBMC were identified, then analysed for reactivity with cultured low density DC. The mAb CMRF-56 (IgG$_1$) labelled a cell population within these DC preparations and was characterised as described below.

CMRF-56 Reactivity with Normal Haemopotetic Non-DC Populations

Cell surface expression of the CMRF-56 antigen on isolated blood and tonsil leucocyte populations was analysed by both single and double labelling in conjunction with flow cytometry. The CMRF-56 mAb did not react with circulating PBMC (n=5), peripheral blood granulocytes (n=3, FIG. 1A), the CD3$^+$ population within ER$^-$PBMC preparations (n=4, FIG. 1A) or the CD16$^+$, CD14$^+$ and CD19$^+$ populations within ER$^-$PBMC preparations (n=6) (FIG. 1A).

Figure 1C:
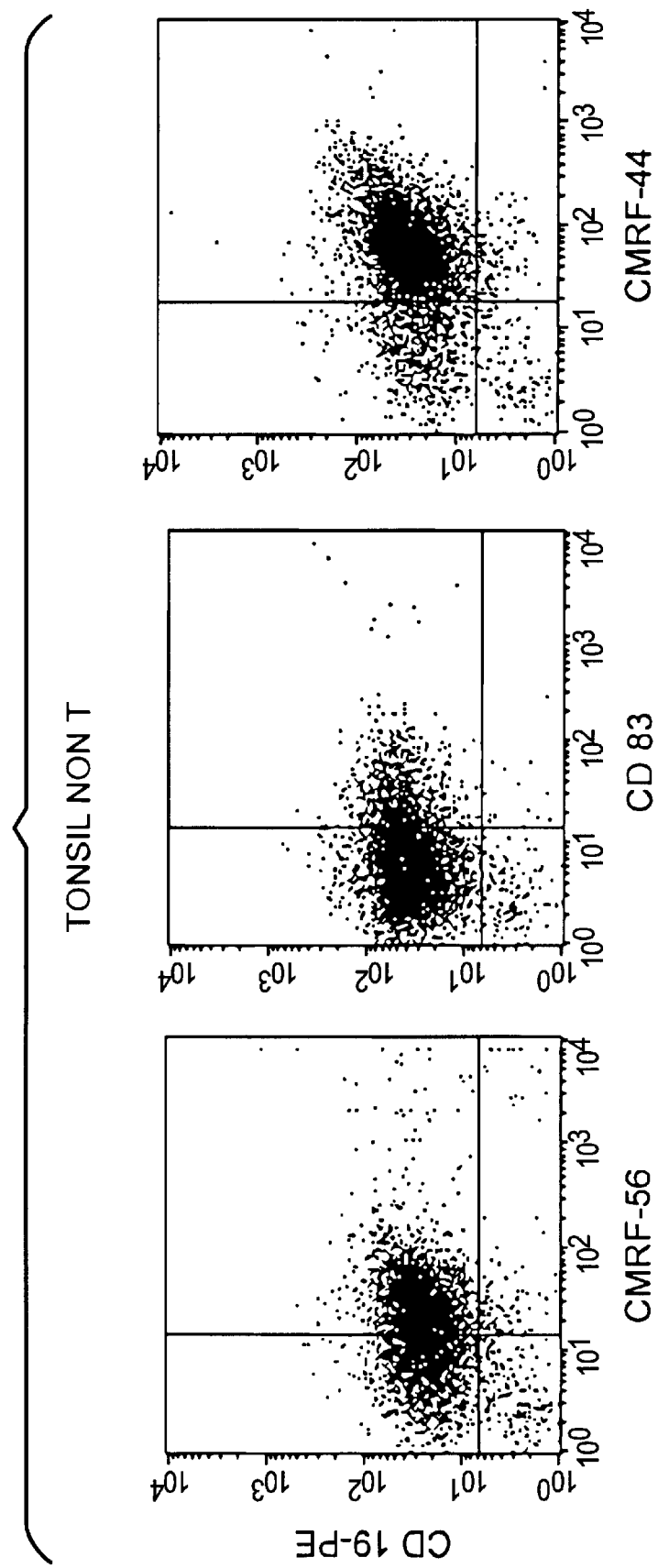

In vitro culture (16 h, 37° C.) of ER$^+$PBMC (n=3) for 24 and 72 h in medium or medium supplemented with PHA or PMA+Cal (n=3) did not induce CMRF-56 antigen expression on the CD3$^+$ population. Culture of ER$^-$PBMC in medium (16 h, 37° C.) induced the expression of the CMRF-56, CD83 and CMRF-44 antigens on a subpopulation of the CD19$^+$ population whereas the CD19$^-$ population (including CD14$^-$ monocytes) lacked these antigens (FIG. 1B).The culture of ER$^-$ and ER$^+$ preparations in the presence of PMA/Cal induced CMRF-56 and CD83 expression on the CD19$^+$ cells present. Culture of ER$^-$ PBMC for 24 h and 72 h in medium supplemented with additional LPS, IFN$\gamma$, GM-CSF or TNF$\alpha$ failed to induce the expression of CMRF-56 on the CD14$^+$ monocyte population despite the induction of changes in CMRF-44 or MHC class II antigen expression (data not shown, n=3). Analysis by flow cytometry of isolated tonsillar lymphocytes confirmed that CMRF-56 did not label with tonsil T lymphocytes (n=4) but, in common with CD83 and CMRF-44, did label a proportion of the tonsil B lymphocytes with moderate intensity (FIG. 1C).

In all tonsil lymphocyte preparations analysed (n=5) there was a clear difference in the percentage of B lymphocytes labelling with the mAb: the CMRF-44 antigen was expressed on a higher percentage and the CD83 antigen on a lower percentage of cells than the CMRF-56 antigen.

Reactivity with Cell Lines and Transfectants

Figure 2A:
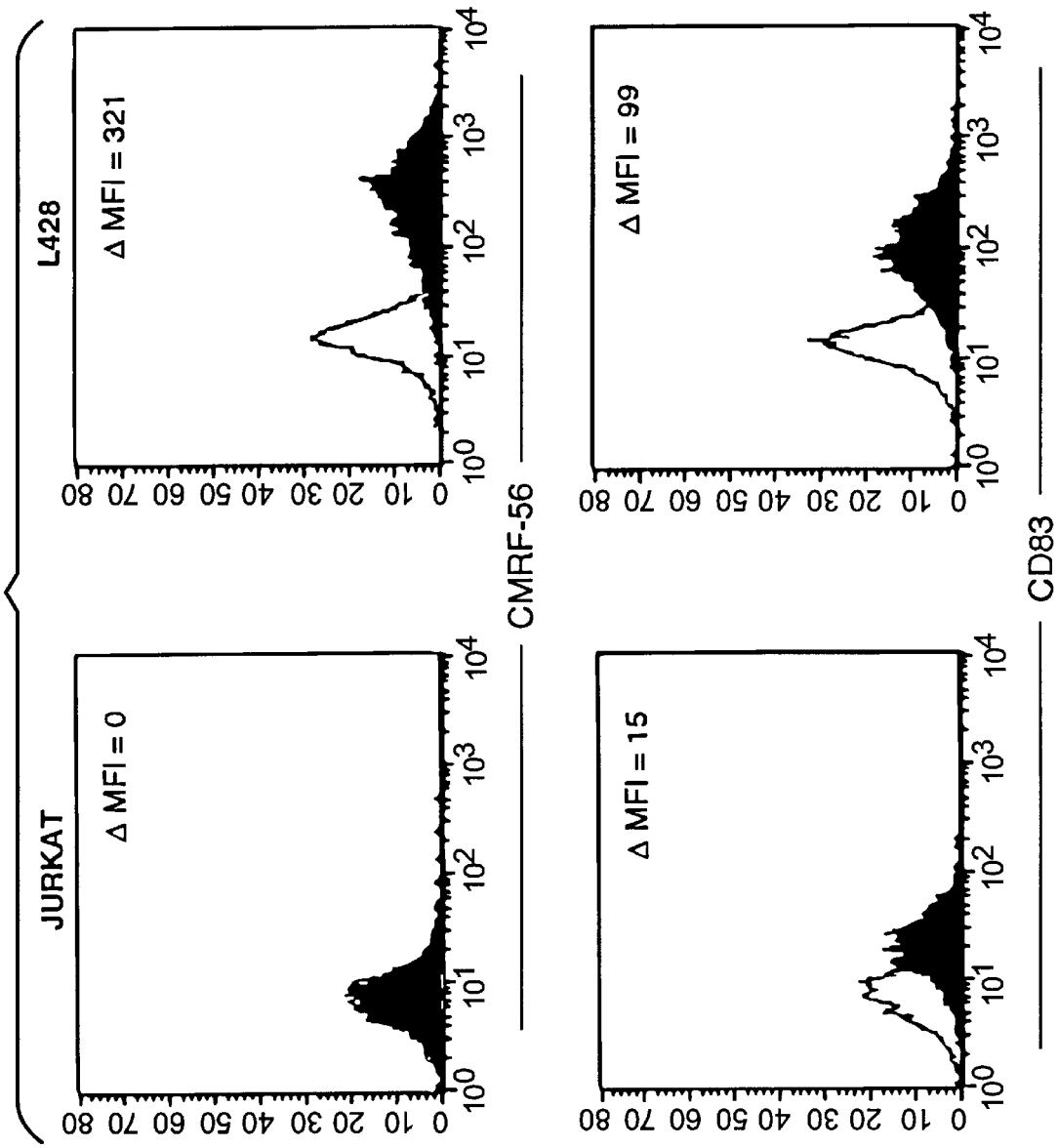
FIG. 2 shows the reactivity of CMRF-56 and HB15 (CD83) with human cell lines and CD83 Cos cell transfectants (A) Data for the human cell lines L428 and Jurkat are shown as immunofluorescent profiles obtained following labelling with either isotype controls ( - - - ), CMRF-56 or CD83 ( - - - ) and are from a representative experiment of six performed. The intensity of CMRF56 and HB15 labelling (MFI) over that of the negative controls is shown in the right hand corner of each histogram of the human cell lines. (B) Data for the COS cell transfectants are shown as the immunofluorescent profiles obtained following labelling of either control transfectants ( - - ) or CD83 transfectants ( - - - ) with CMRF-56 or CD83. Data are from a representative experiment of three performed.
Figure 2B:
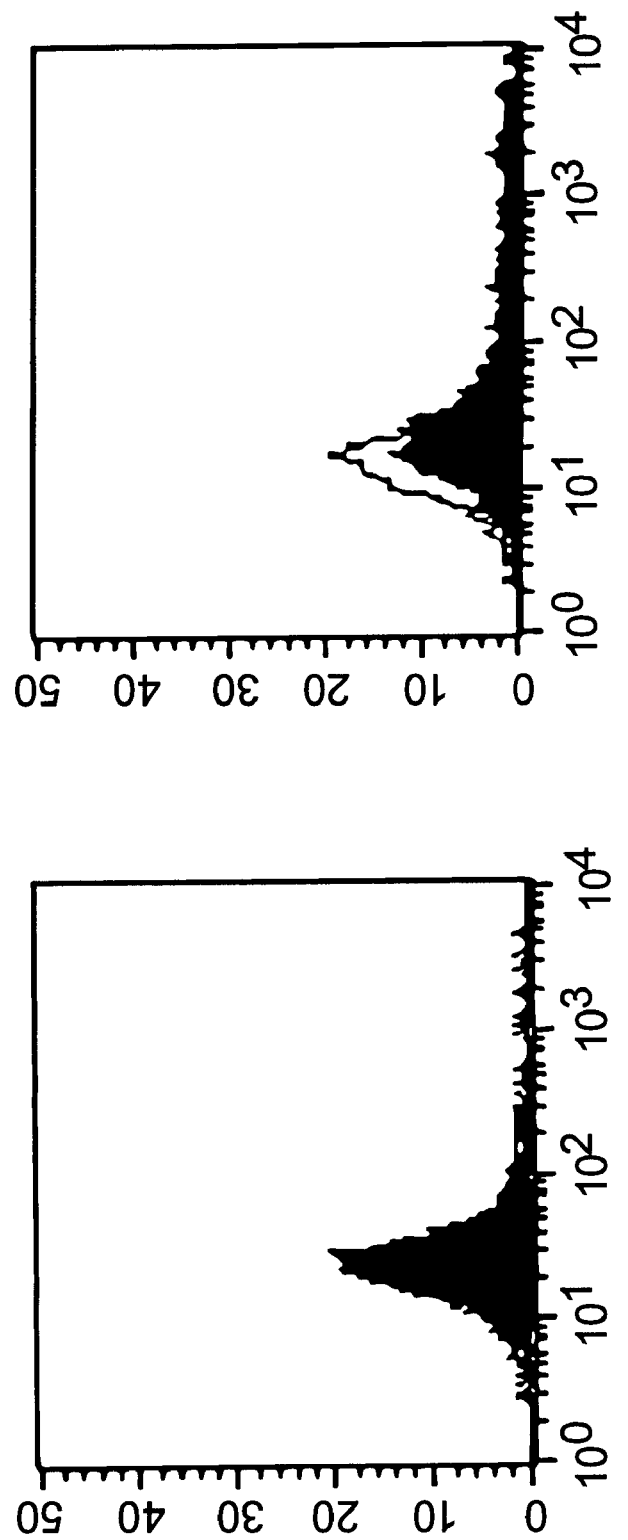

The cell surface expression of CMRF-56 on human cell lines was analysed by flow cytometry. The CMRF-56 antigen was expressed at detectable levels on a number of B cell lines (Mann, RaJi,) and HD-derived cell lines (L428, KM-H2, HDLM-2) with the strongest staining noted on the L428 (FIG. 2A) and Mann cell lines. Cell lines that did not express detectable levels of CMRF-56 antigen included the myelo-erythroid K562 line, the T lymphoid lines HSB2 and Molt 4, the myeloid monocytoid cell lines NB4, THP1, U937, KG1 and KG1a and the pre B lymphoid line NALM6. The CMRF-56 mAb did not react with the CD83$^+$ T lymphoid cell line Jurkat (FIG. 2A) and as shown in FIG. 2B did not label CD83 positive COS cell transfectants (n=3).

The CMRF-56 antigen showed significant capping on a proportion of L428 cells by CMRF-56 mAb FITC-SAM. The CD83 antigen was also capped by HB15/PE-SAM into discrete patches on 60% of stained cells. Of the cells capped with CMRF-56 and subsequently stained with CD83, a proportion showed residual evenly distributed CD83 staining of the membrane indicating independent membrane molecular localisation of the two antigens.

Biochemical Analysis

Figure 3:
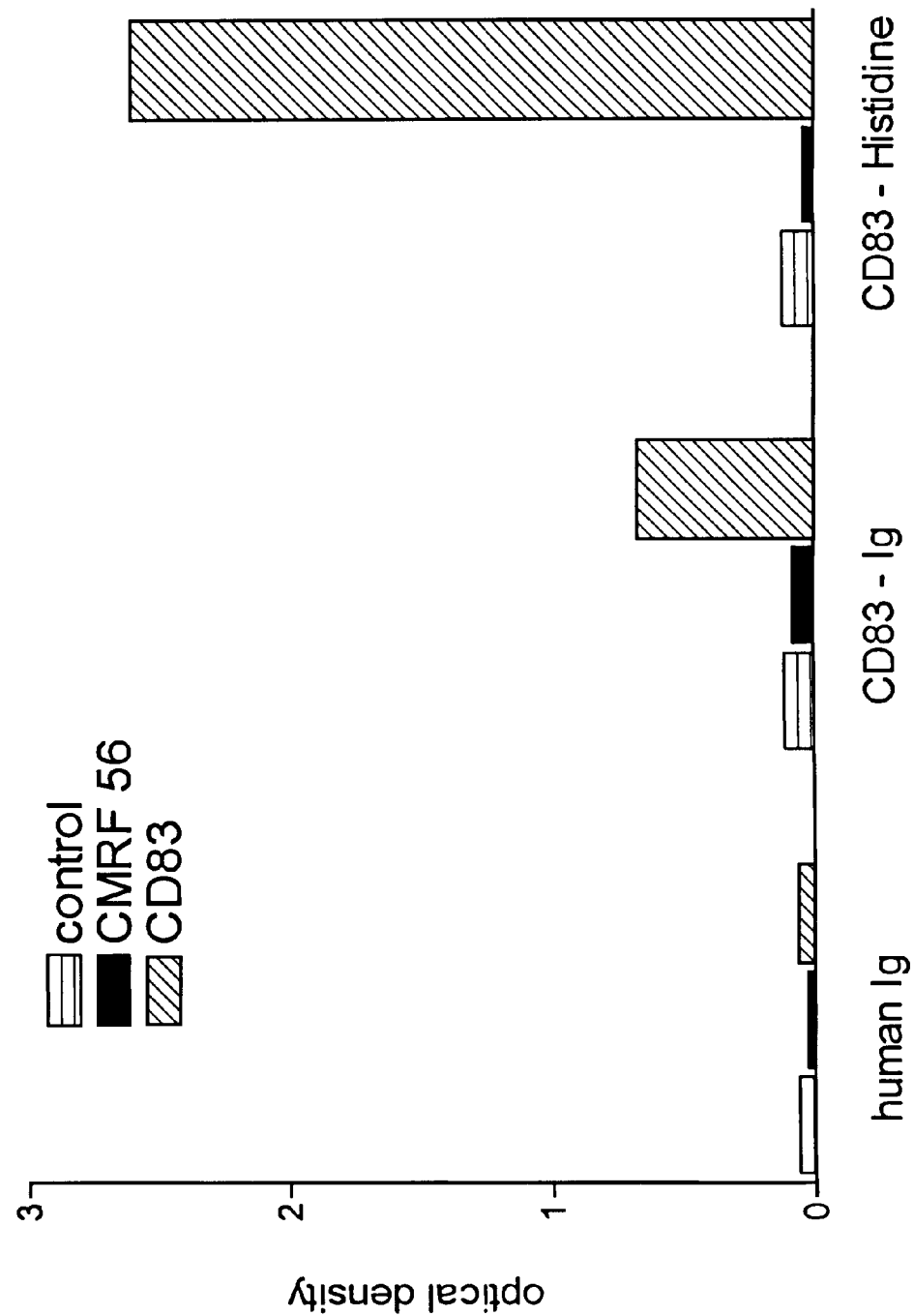
FIG. 3 characterises the CMRF-56 antigen. Binding of CMRF-56, CD83 and negative control mAb to human Ig, CD83-Ig and CD83-histidine as analysed by ELISA. Data are shown as histograms and are from a representative experiment of three performed.

The sensitivity of CMRF-56 antigen to enzyme digestion or blockage of n-linked glycosylation was examined by flow cytometry. Increased binding of the CMRF-56 mAb to L428 cells was observed following treatment of the cells with either neuramnidase (1.5 fold increase, sd=0.2, n=5) or pronase (1.4 fold increase, sd=0.25, n=4). Preincubation with tunicamycin did not significantly alter observed binding. Immunostaining of L428 detergent lysates applied to NC membranes demonstrated that the CMRF-56 antigen was effectively solubilised by the non-ionic detergent TRITON X-100 and the zwitteronic detergent CHAPS. Numerous immunoprecipitation experiments from lysates prepared following L428 cell surface protein (biotin), cell surface sialic acid (biotin hydrazide) or metabolic ($^{35}$S) labelling failed to identify the CMRF-56 antigen despite co-precipitation of appropriate molecular weight products with the anti-MHC class II and CD83 reagents (data not shown). Western blotting of L428 and Mann cell line lysates similarly failed to identify the CMRF-56 antigen. Immunostaining of L428 lipid and non-lipid extracts applied to nitrocellulose membranes did not detect CMRF-56 antigen in either fraction, suggesting that the CMRF-56 antigen epitope is sensitive to organic solvents (data not shown). The reactivity of CMRF-56 with both CD83-Ig and CD83-hist constructs was analysed by ELISA (FIG. 3). In contrast to the CD83 mAb, CMRF-56 did not bind to either the CD83 Ig (n=3) or the CD83-hist recombinant material (n=3).

CMRF-56 Reactivity with Isolated DC

The reactivity of CMRF-56 with isolated DC populations was examined by indirect immunofluorescence and flow cytometry.

Directly isolated fresh DC (FIG. 5A) did not express detectable levels of either the CMRF-56 or CD83 antigens. However expression of both antigens was rapidly induced on directly isolated DC within 6 hrs of in vitro culture. In contrast, expression of the CMRF-44 antigen was consistently detected on a subpopulation of directly isolated DC and further upregulation of the CMRF-44 antigen preceded that of both the CMRF-56 and CD83 antigens.

Analysis of the DC enriched low density fraction of cultured ER$^-$PBMC invariably identified a subpopulation of CMRF-56$^+$ cells (10–30%, n=20) identical to the DC populations detected by CD83 and CMRF-44 (FIG. 4A). Double labelling (FIG. 4B) confirmed that the CMRF-56 reactivity was associated with the lin$^-$, CMRF-44$^+$ and CD83$^+$ DC populations. FACS sorting of low density ER$^-$PBMC on the basis of CMRF-56 expression clearly demonstrated that potent allostimulatory activity was associated with the CMRF-56$^+$ population and that the CMRF-56$^-$ population was only weakly stimulatory (n=3, FIG. 4C). Binding of the mAb did not affect the DC allostimulatory activity.

Figure 6A:
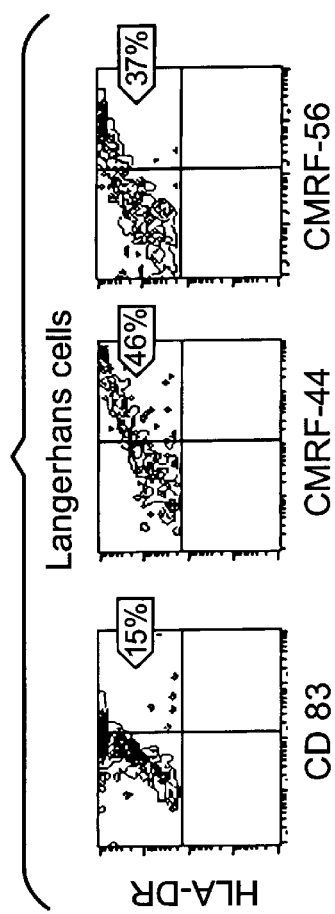
FIG. 6 shows CMRF-56 and CD83 reactivity with (A) isolated LC (B) isolated dermal DC and (C) in vitro generated DC. LC and dermal DC preparations were double labelled with CMRF-56, CMRF-44 and CD83 vs HLA-DR. In vitro generated DC were double labelled with anti-CD1a, CMRF-44 and CMRF-56 vs CD14-PE. In all cases, the gates delineating positive staining were set on the basis of negative control staining. The percentages shown on the right of each dot plot indicate the percentage of either LC, dermal DC or in vitro generated DC that expressed the relevant antigen. Data are from representative experiments of three performed with each type of cell preparation.
Figure 6B:
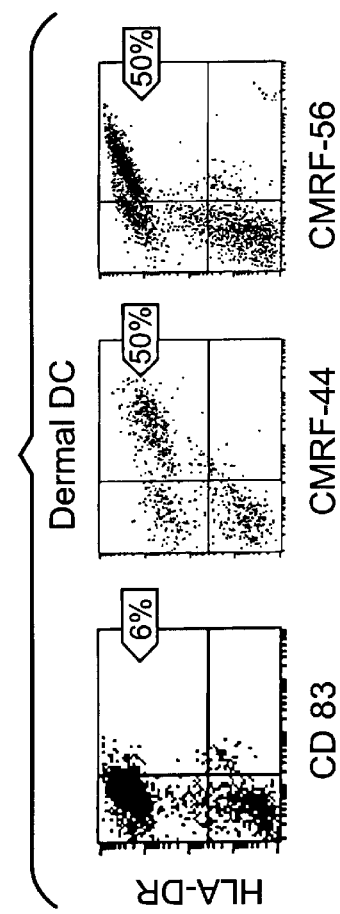

Flow cytometric analysis of isolated LC (n=3) demonstrated that approximately 40% of these cells express the CMRF-56 and CMRF-44 antigens at high density, with CD83 being expressed weakly on a significantly lower percentage of cells (FIG. 6A). Dermal DC (n=3), although strongly CMRF-44 and CMRF-56 positive, showed only weak staining of a subpopulation of cells with CD83 (FIG. 6B).

Figure 7B:
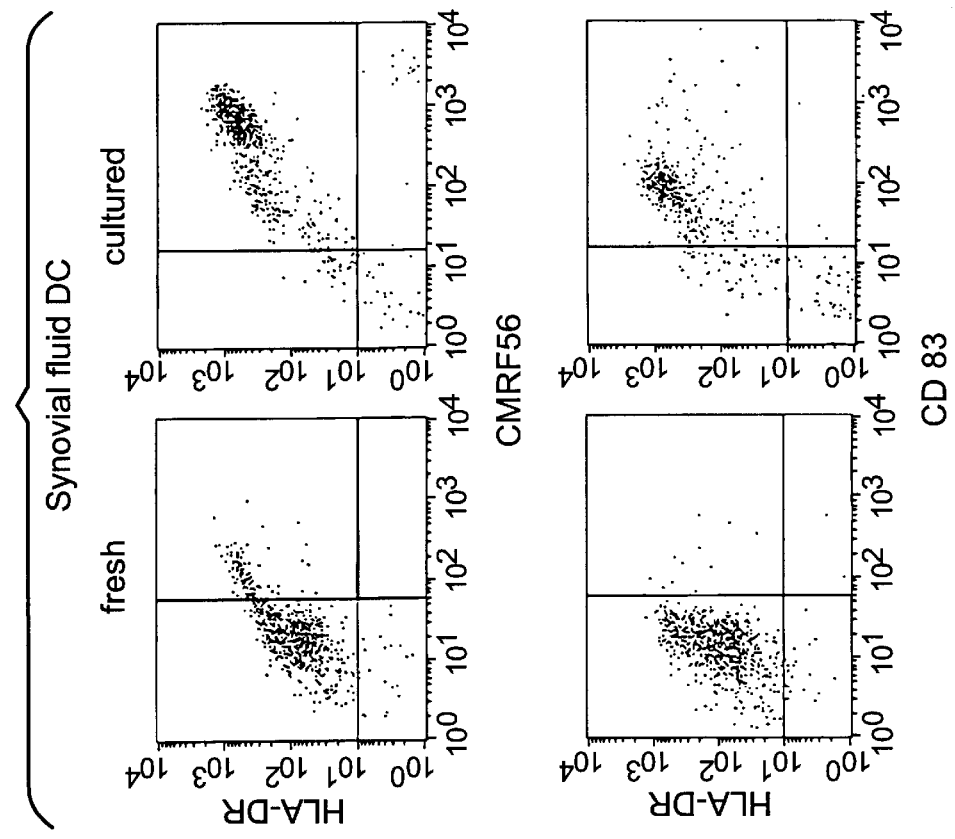
FIG. 7 shows CMRF-56 and CD83 reactivity with isolated SF-DC and tonsil DC, before and after in vitro culture. Preparations of (A) Tonsil DC and (B) SF-DC were double labelled with CMRF-56, CD83/FITC SAM vs HLA-DR-PE before and after 16 hr culture in medium. In all cases gates delineating positive staining were set on the basis of negative control staining. Data are from representative experiments of three performed on each type of DC preparation.
Figure 7A:
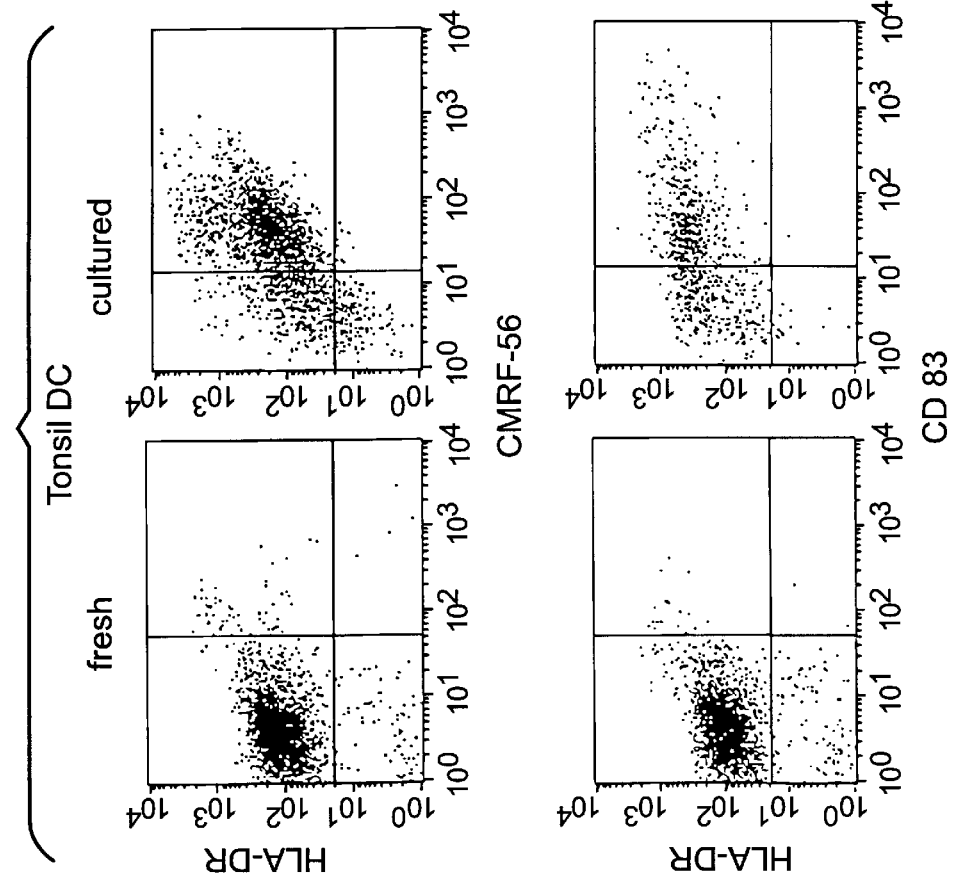

Directly isolated SFDC, although lacking the CD83 antigen, contained a subpopulation of CMRF-56$^+$ cells (n=5, FIG. 7A). Following in vitro culture of these SF DC preparations further upregulation of both the CMRF-56 and CD83 antigens was observed.

Tonsil DC prepared by direct immunodepletion were, in common with freshly isolated blood DC, CD83 and CMRF-56 negative but expressed both antigens in high density after a period of in vitro culture (n=5, FIG. 7B).

Figure 6C:
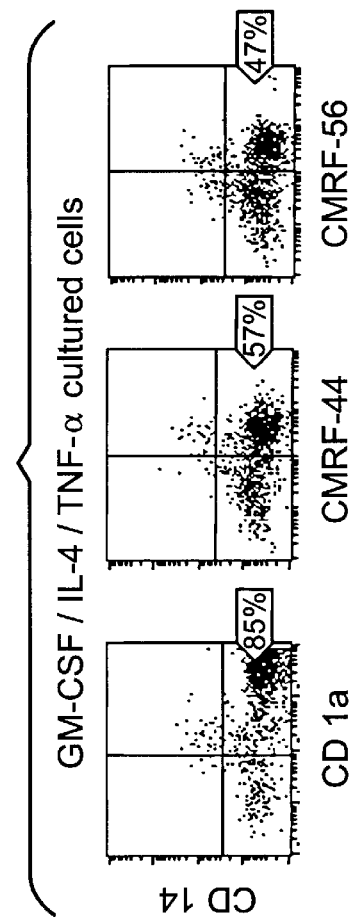

In vitro generated Mo-DC populations were also studied (n=3). Following culture of monocytes in the presence of GM-CSF. L-4 and TNFα the resulting Mo-.DC were strongly CMRF-56+. The percentage of CMRF-56+ cells was significantly less than the percentage of CD1a+ positive cells (FIG. 6C).

Immunohistological Analysis of CMRF-56 Expression

Immunohistological staining of lymph node and tonsil sections detected weak CMRF-56 antigen expression on the germinal centre lymphocytes. and strong expression on scattered interfollicular (T zone) cells. Immunofluorescent double labelling of tonsil sections demonstrated that the CMRF-56 positive interfollicular cells lacked CD 19 and CD20 but expressed CD86. Double labelling with CMRF-56 and CD83 demonstrated that within the interfollicular regions CMRF-56 antigen was expressed on a lower number of cells than CD83 and that a subpopulation of the CMRF-56 positive population did not express CD83.

DISCUSSION

Characterisation of the mAb CMRF-56 has established that it recognises a previously undefined antigenic epitope with restricted expression on human DC populations. Circulating blood leucocytes did not express the CMRF-56 antigen and following either culture alone or in vitro activation. CMRF-56 antigen expression was detected only within the low density (DC enriched) fraction of cultured PBMC and on a subpopulation of CD19+ lymphocytes. Immunolabelling and FACS sorting of the low density fraction of cultured PBMC confirmed that CMRF-56 was staining the DC population within these preparations. The finding that circulating blood DC are CMRF56 but express the antigen in high density within 6 h culture confirmed that CMRF-56 recognises a early differentiation/activation marker on DC. The CMRF-56 antigen was also expressed on other DC populations including isolated LC and dermal DC. Rapid upregulation of the CMRF-56 antigen on tonsil and Synovial fluid DC occurred after a short period of in vitro culture. The CMRF-56 antigen can be clearly distinguished from the CMRF-44 on the basis of its absense from CMRF-44+ cells eg. in vitro cultured and IFNγ activated monocytes as well as freshly isolated blood DC. Likewise, the lack of CMRF-56 reactivity with CD83 transfectants, CD83 recombinant proteins and the CD83+ cell line Jurkat clearly distinguished these two antigens. At present the only selective DC surface markers available are CMRF-44[13,20] and CD83[18,19], which also recognise early activation markers on DC. The CMRF-44 antigen, but not the CD83 and CMRF-56 antigens, is expressed on a subpopulation of circulating DC[31]. Although all three markers are rapidly upregulated on DC with culture, as shown in this study upregulation of CMRF-44 on isolated blood DC, clearly precedes that of CMRF-56 and CD83 antigens. Analysis of isolated dermal DC, LC, synovial fluid DC and tonsil DC suggests that expression of the CMRF-56 antigen precedes CD83 expression on these populations.

Thus it appears that these three distinct DC differentiation/activation antigens upregulate in the order of CMRF-44 antigen, CMRF-56 antigen and then the CD83 antigen. However, this interpretation may be influenced by the fact that the expression of the CMRF-44 and CMRF-56 antigens on isolated DC is maintained throughout a short period of in vitro culture, whereas in some experiments the surface CD83 antigen labelling decreases after 24 h. This downregulation of CD83 antigen expression may be due to the cleavage of surface protein and release of soluble CD83 which has been reported to occur with activated B lymphocytes[36].

CMRF-56 and CD83 differed considerably in terms of their reactivity with IDC in tonsil sections. Double labelling demonstrated that the CMRF-56 antigen was expressed. on a considerably lower number of cells than CD83 in the interfollicular zone and that populations of both CMRF-56+/CD83+, CMRF-56−/CD83+ and CMR-56+, CD83− cells were present. Previous studies have demonstrated that CD83 is expressed by a subset of IDC within tonsil tissue. The expression of the CMRF-56 antigen on a CD19−, CD20−, HLA-DR+ population within the interfollicular zone that includes a population of CD83 cells provides further evidence that the CMRF-56 and CD83 antigens are expressed at different stages of DC differentiation/activation. However, the absence of CMRF-56 antigen on a subpopulation of CD83+ IDC contrasts with the results obtained using isolated tonsil DC populations. Thus CD83+. CMRF-56− DC populations were not detected in any of the preparations analyzed either before or after in vitro culture. This may in the case of isolated tonsil DC reflect the difficulty in isolating all the cell populations from the tissue particularly without exposing the isolated cells to in vitro enzyme digestion. Interestingly, although the majority of germinal centre B cells expressed low density CMRF-56 and CD83 antigens when analysed in situ, only a subpopulation of isolated tonsillar B cells expressed these antigens, suggesting that the release of B cells from the tissue matrix may be unrepresentative.

CMRF-56 expression on human cell lines parallels that of the CMRF-44 and CD83 antigens, in many respects being restricted to HD derived and B cell lines whereas cell lines of myeloid origin lack these antigens. A similar pattern is observed following activation of ER−PBMC or ER+PBMC populations, with expression of CMRF56 and CD83 being readily inducible on B lymphocytes. Although all blood B lymphocytes express these antigens following in vitro activation, these antigens have distinctly different levels of expression on isolated tonsil lymphocytes, CD83 being expressed on a considerably lower percentage of B lymphocytes than CMRF-56, whilst CMRF-44 had considerably higher expression.

Negligible expression of these antigens on the CD14− monocyte population was observed using a range of single stimuli. Nonetheless, CD83 expression and CMRF-44 can be induced on cells of myeloid origin following long term culture in the presence of particular cytoidne combinations. These cells closely resemble DC in terms of function and phenotype and as shown in this study In vitro these Mo-DC also express the CMRF-56 antigen.

It is clear that the specificity of CMRF-56 and CD83 for DC populations is not absolute, but the study of these antigens in conjunction with B lymphocyte markers provides a highly selective means of identifying DC populations at an early stage of activation, both in situ and within isolated leucocyte populations. The upregulation of these molecules is associated with a phase of significant activation of DC function. Thus, these DC upregulate the costimulator molecules CD80, CD86[30,32,19,14,43], CD40[33] and adhesion molecules such as ICAM-1[7,44].

In summary, the CMRF-56 antigen is as are the other associated antigens CMRF-44 and CD83 expressed on the L428 cell line. Nonetheless, the serological data provided clearly distinguishes the CMRF-56 antigenic epitope from the CMRF-44 antigen. The CD83 antigen which at a serological level has some parallels with the CMRF-56 antigen is clearly distinguished from it as a cell surface protein that caps independently of CMRF-56 antigen. Further evidence was obtained for the distinct nature of these two antigens by demonstrating that mAb CMRF-56 did not bind CD83transfected cells or recombinant material. Thus mAb CMRF-56 becomes a further mAb with specificity for DC.

The CMRF-56 mAb does not label cytoline or LPS stimulated blood monocytes over the 48 hr period of observation. This makes CMRF-56 mAb perhaps particularly useful as a reagent for determining committed monocytic cells from committed DC precursors. It is clear that the CMRF-56 antigen upregulates as part of the DC activation/differentiation pathway. The kinetics of upregulation documented in FIG. 5 suggest the CMRF-56 antigen is expressed later than CD83 but persists larger than CD83 which appears to down regulate after 48 hrs.

INDUSTRIAL APPLICATION

There are a number of uses to which the antibodies of the invention (which recognise and bind to the activation antigen CMRF-56) can be put. Such uses include (1) the identification (for diagnostic purposes) of activated DC; and (2) the purification/concentration of activated DC, and these uses accordingly represent further aspects of this invention.

Diagnostic applications of the present exemplary mAb CMRF-56 include allowing for assessment of activated (CMRF-56 positive) against non-activated (CMRF-56 negative) DC, which may be of use in the diagnosis and/or therapy of diseases such as cancer.

In such applications, any immunological-based assay procedures known in the art could be employed for quantifying the amount of activated DC in a sample. Such procedures are summarised in TiJssen[24] such as flow cytometry. ELISA, RIA and fluorescence microscopy among others.

In terms of isolation of activated DC, once again any process or purification system which employs the antibodies (or their binding fragments) as the primary immunological reagent can be used. Many such processes are known, as are purification systems which allow for these processes to be put into effect. An example of a commercially available purification system is the avidin-biotin immunoaffinity system[29] from CellPro, Inc., Washington, USA. See also U.S. Pat. Nos. 5,215.927, 5,225,353, 5,262,334, 5,240,856 and PCT/US91/07646 published Apr. 30, 1992, all incorporated herein by reference. This system employs directly or indirectly a biotinylated monoclonal antibody directed against a target cell and a column containing immunobilized avidin and can be readily adapted to extract activated human dendritic cells, in this case from human peripheral blood, using the exemplary mAb CMRF-56 as follows:

1. A sample of human peripheral blood containing the human dendritic cells is mixed with biotinylated mAb CMRF-56 and incubated to allow formation of mAb CMRF-56/human DC complexes.
2. Following incubation, the mixture is introduced into a CellPro continuous-flow immunoadsorption column filled with avidin-coated beads, the strong affinity between biotin and avidin causing the biotin-coated mAb CMRF-56 (together with the human DC to which they have bound) to adhere to the avidin-coated beads.
3. After unwanted cells present in the mixture are washed away, captured activated human DC are removed from the column by gentle agitation and are available for use.

Variations on this theme using mAb CMRF-56 as primary antibody (to bind to activated DC) and a biotinylated secondary antibody (to bind to mAb CMRF-56) can also be employed.

It will be appreciated that before admixture with mAb CMRF-56 in accordance with the above protocol, the human peripheral blood sample should be treated to ensure that the DC the sample contains are activated. This can easily be achieved by, for example, overnight incubation of the sample.

For use in the above protocol, mAb CMRF-56 can be biotinylated by any one of a number of conventional methods. For example, the biotinylation procedure of Berenson et al[29] can be employed.

A possible and preferred preliminary step in the methods outlined above is the enrichment of DC in the sample by gradient centrifugation[25-27]. While this optional enrichment step can employ any suitable known gradient medium (such as albumin or metrizamide), it is however preferred that a Nycodenz medium (Nycomed Pharma, Oslo, Norway) be used[28] in relation to 16 hour cultured T lymphocyte-depleted peripheral blood mononuclear cells. The applicants have found that use of this gradient reliably yields a population of low density cells that is highly enriched for DC.

It will be apparent to one skilled in the art that there are numerous other means of immunoselection of dendritic cells, in addition to avidin-biotin immunoaffinity chromatography. These include, but are not limited to, immunoselection using magnetic beads, ferrofluids, dipsticks, petri dishes, and a wide variety of other solid phases that can be derivatized so as to specifically bind mAb CMRF-56 labelled DC.

Once purified/concentrated by the above or any other suitable process, the activated DC can be employed in research or in commercial applications. One such potentially commercial application for activated DC is as part of an immunopotentiating composition together with an antigen protective against disease, for either prophylaxis or therapy. It is believed that such compositions would increase both the speed and efficiency of the immune response generated against the protective antigen.

Other applications of the activated DC will of course be apparent to those persons skilled in this art.

Another contemplated application of the mAb CMRF-56 is in targeting activated DC in patients to induce immunosuppression.

It will be understood that the above description is exemplary only and that the present invention is not limited thereto.

DEPOSIT

Hybridoma CMRF-56 (produced using myeloma cell line NS-1) has been deposited to provide supplemental disclosure of the invention. Deposition was with the American Type Culture Collection (ATCC), 10801 University Boulevard, Manassas, Va. 20110-2209, USA as of Oct. 9, 1996 under the terms of the Budapest Treaty. All restrictions upon public access to this deposit will be irrevocably removed upon the grant of the patent and the deposit will be replaced if viable samples cannot be dispensed by the Depository. Hybridoma CMRF-56 has been given ATCC Accession No. 12202.

REFERENCES

1. Steinman, R. M. 1991 . The dendritic cell system and its role in immunogenicity. *Ann. Rev. Immunol.* 9:271.
2. Macpherson, G. G. 1989. Lymphoid dendritic cells: their life history and roles in immune responses. *Res. Immunol.* 140:877.

3. Hart, D. N. J. and J. L. McKenzie. 1990. Interstitial dendritic cells. *Intern Rev Immunol.* 6:127.
4. Steinman, R. M., B. Gutcbinov, M. D. Witmer, and M. C. Nussenweig. 1983. Dendritic cells are the primary stimulators of the primary mixed lymphocyte reaction in mice. *J. Exp. Med.* 147:613.
5. Inaba, K., M. D. Witmer-Pack, and R. M. Steinman. 1984. Clustering of dendritic cells, helper T lymphocytes and histocompatibaility B cells during primary T cell responses in vitro. *J. Exp. Med.* 160.858.
6. Kuntz Crow, M. and R. G. Kunkel. 1982. Human dendritic cells: major stimulators of the autologous and allogeneic mixed leucocyte reactions. *Clin. Exp. Immunol.* 49:338.
7. Thomas, R., L. S. Davis, and P. E. Lipsky. 1993. Isolation and characterization of human peripheral blood dendritic cells. *J Immunol* 150:821.
8. Hart, D. N. J., and J. L. McKenzie. 1988. Isolation and characterization of human tonsil dendritic cells. *J Exp Med* 168:157.
9. Prickett, T. C. R., J. L. McKenzie, and D. N. J. Hart. 1992. Adhesion molecules on human tonsil dendritic cells. *Transplantation* 53:483.
10. Freudenthal, P. S., and R. M. Steinman. 1990. The distinct surface of human blood dendritic cells, as observed after an improved isolation method. *PNAS* 87:7698.
11. Hart, D. N. J., and T. C. R. Prickett. 1993. Intercellular adhesion molecule-2 (ICAM-2) expression on human dendritic cells. *Cellular Immunol.* 148:447.
12. Hsu, P. L. and S. M. Hsu. 1990. Identification of an Mr 70,000 antigen associated with Reed-Sternberg cells and interdigitating reticulum cells. *Cancer Res.* 50:350.
13. Zhou, L. J, R. Schwarting, H. M. Smith, and T. F. Tedder. 1992. A novel cell surface molecule expressed by human interdigitating reticulum cells, Langerhans cells, and activated lymphocytes is a new member of the Ig superfamily. *J. Immunol.* 149:735.
14. Hart, D. N. J., G. C. Starling, V. L. Calder, and N. S. Fernando. 1993. B7/BB-1 is a leucocyte differentiation antigen on human dendritic cells induced by activation. *Immunol* 79:616.
15. McKenzie, J. L., W. Egner, V. L. Calder, and D. N. J. Hart. 1992. Hodgkin's disease cell lines: a model for interleukin-1-independent accessory cell function. *Immunol* 77:345.
16. Kadin, M. E. 1982. Possible origin of the Reed-Sternberg cell from an interdigitating reticulum cell. *Cancer Treat. Rep.* 66:601.
17. Hsu, S. M. 1990. The never ending controversies in Hodgkin's disease. *Blood* 75:1742.
18. Zhou, L., Schwarting, R., Smith, H. M., and Tedder, T. F. (1992) A novel cell-surface molecular expressed by human interdigitating reticulum cells, Langerhans cells, and activated lymphocytes is a new member of the Ig superfamily. *J. Immunol* 149:735.
19. Zhou, L., and Tedder, T. F. (1995) Human blood dendritic cells selectively express CD83, a member of the Immunoglobulin superfamily. *J. Immunol* 154:3821.
20. Hock, B. D., Starling, G. C., Daniel, P. B., and Hart, D. N. J. (1994) Characterisation of CMRF-44, a novel monoclonal antibody to an activation antigen expressed by the allostimulatory cells within peripheral blood, including dendritic cells. *Immunol* 83:573.
21. Kohler G. and Milstein C. (1975) Continuous Cultures of Fused Cells Secreting Antibody of Predefined Specificity. *Nature* 256:495–497.
22. Tjissen P. (1990) Practice and Theory of Enzyme Immunoassays. *Laboratory Techniques in Biochemistry and Molecular Biology*, Elsevier, Amsterdam, New York, Oxford 117–121.
23. Hodgson J. (1991) Making Monoclonals in Microbes. *Biotechnology* 9:423–425.
24. V. Diehl, H. H. Kirchner, H. Burrichter, H. Stein, C. Fonatsch, J. Gerdes, M. Schaadt, W. Heit, B. Uchanska-Ziegler, A. Ziegler, F. Heitz and K. Sueno. (1982) Characteristics of Hodgkins Disease-Derived Cell Lines. *Cancer Treat Rep.* 66:615–632.
25. Van Voorhis, W. C., Hair L., Steinman K., Kaplan G. (1982) Human Dendritic Cells. *J. Exp. Med.* 155:1172.
26. Knight S. C., Farrant J. Bryant A., Edwards A. J., Burman S., Lever A., Clark J., Webster A. D. B. (1986) Non-adherent low density cells from human peripheral blood contain dendritic cells and monocytes both with vieled morphology. *Immunology* 57:595.
27. Young J. W., Steinman R. M. (1988) Accessory cell requirements for the mixed leukocyte reaction and polyclonal mitogens as studied with a new technique for enriching blood dendritic cells. *Cellular Immunology* 111:167.
28. Boyum A. (1983). Isolation of human blood monocytes with Nycodenz, a new non-ionic iodinated gradient medium. *Scand J. Immunology* 17, 429–436.
29. Berenson R. J., Bensinger W. I., Kalamz D. (1986) Positive selection of Viable Cell Populations Using Avidin-Biotin Immunoadsorption. *Journal of Immunological Methods* 91:11.
30. O'Doherty U, Steinman R M, Peng M, Cameron P U, Gezelter S. Kopeloff I, Swriggard W J, Pope M. Bardwaj N: Dendritic cells freshly isolated from human blood express CD4 and mature into typical immunostimulatory dendritic cells after culture in monocyte-conditioned medium. *J Exp Med* 178:1067, 1993.
31. Fearnley D B, McLellan A D, Mannering S I, Hock B D, Hart D N J: Isolation of human blood dendritic cells using the CMRF-44 monoclonal antibody: implications for studies on antigen presenting cell function and immunotherapy. *Blood* 89:3708, 1997.
32. McLellan A D, Starling G C, Williams L A, Hock B D, Hart D N J: Activation of human peripheral blood dendritic cells induces the CD86 costimulatory molecule. *Eur J Immunol* 25:2064, 1995.
33. McLellan A D, Sorg R V, Williams L A. Hart D N J: Human dendritic cells activate T lymphocytes via a CD40:CD40 ligand-dependent pathway. *Eur J Immunol* 26:1204, 1996.
34. Williams L A, Hock E D, Hart D N J: Human T lymphocytes and haemopoietic cell lines express CD24 associated carbohydrate epitopes in the absence of CD24 mRNA or protein. *Blood* 88.3048, 1996.
35. Egner W. Andreesen R. Hart D N J: Allostimulatory cells in fresh human blood: heterogeneity in antigen presenting cell populations. *Transplantation* 56:945, 1993.
36. McLellan A D, Starling G C, Hart D N J: Isolation of human blood dendritic cells by Nycodenz discontinuous gradient centrifugation. *J Immunol Methods* 184:81, 1995.
37. Peguet-Navarro J. Dalbiez-Gauthier C, Rattis F, van Kooten C, Banchereau J, Schmitt D: Functional expression of CD40 antigen on human epidermal Langerhans cells. *J Immunol* 155:4241, 1995.
38. Summers K, O'Donnell J. Williams L A. Hart D N J: Expression and function of CD80 and CD86 costimulator molecules on synovial dendritic cells in chronic arthritic disease. *Arth Rheum* 39:1287, 1996.

39. Daish A, Hock B D, Hart D N J: Characterization of a novel leucocyte activation antigen recognised by the antibody CMRF-37. *Immunol Cell Biol* 72:13, 1994.

40. Kahne T, Ansorge S: Non-radioactive labelling and immunoprecipitation analysis of leukocyte surface proteins using different methods of protein biotinylation. *J Immunol Methods* 168.209, 1994.

41. Schuh R, Kremmer E, Ego E, Wasiliu M, Thierfelder S: Determination of monoclonal antibody specificity by immunoadsorption and Western blotting. *J Immunol Methods* 152:59, 1992.

42. Armitage R J, Macduff B M, Ulrich D T, Zappone J, Otten C, Fanslow W C: Evidence for a functional role of CD83 in T- and B- cell responses. *Tissue Antigens* 48:453, 1996 (abstr.).

43. Thomas R, Davis L S, Lipskey P E: Comparative accessory cell function of human peripheral blood dendritic cells and monocytes. *J Immunol* 151:6840, 1993.

44. Starling G C, Egner W, McLellan A D, Fawcett J, Simmons D L, Hart D N J: Intercellular adhesion molecule-3 is a costimulatory ligand for LFA-1 expressed on human blood dendritic cells. *Eur J Immunol* 25:2528, 1995.

What is claimed is:

1. An isolated monoclonal antibody CMRF-56 produced by hybridoma ATCC HB 12202 that binds activated dendritic cells (DC).

2. The isolated antibody of claim 1 wherein the antibody binds to an antigen on activated DC which antigen binds to monoclonal antibody CMRF-56 produced by hybridoma ATCC HB 12202.

3. A hybridoma cell line having Accession No. ATCC HB 12202.

4. A process for purifying activated dendritic cells (DC) from a sample containing said activated DC, said process comprising the steps of contacting said sample with the antibody of claim 1 and then recovering activated DC which have bound to said antibody.

5. A process for identifying activated dendritic cells (DC) in a sample comprising the steps of contacting said sample with the antibody of claim 1 to form an antibody/activated DC complex; and detecting the presence of said antibody/DC complex to identify the activated dendritic cells (DC).

6. The process of claim 4 wherein the CMRF-56 antibody is biotinylated.

7. The process of claim 5 wherein the CMRF-56 antibody is biotinylated.

* * * * *